(12) United States Patent
Greeley et al.

(10) Patent No.: US 11,589,563 B2
(45) Date of Patent: Feb. 28, 2023

(54) PUPAE TRANSFER DEVICE

(71) Applicant: Verily Life Sciences LLC, South San Francisco, CA (US)

(72) Inventors: Daniel Greeley, San Francisco, CA (US); Peter Smith, Pacifica, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 275 days.

(21) Appl. No.: 16/947,162

(22) Filed: Jul. 21, 2020

(65) Prior Publication Data
US 2021/0022325 A1    Jan. 28, 2021

Related U.S. Application Data

(60) Provisional application No. 62/877,973, filed on Jul. 24, 2019.

(51) Int. Cl.
A01K 67/033    (2006.01)
B07B 1/28      (2006.01)
A01K 29/00     (2006.01)

(52) U.S. Cl.
CPC .............. *A01K 67/033* (2013.01); *B07B 1/28* (2013.01); *A01K 29/00* (2013.01); *A01K 2227/706* (2013.01)

(58) Field of Classification Search
CPC .. A01K 67/033; A01K 2227/706; B03B 7/00; B03B 11/00; B07B 1/28; B07B 2230/01
See application file for complete search history.

(56) References Cited

U.S. PATENT DOCUMENTS

| 5,230,646 | A |   | 7/1993  | Thorup |
| 5,295,583 | A | * | 3/1994  | Bischofberger ..... B01D 29/885 |
|           |   |   |         |                           209/21 |
| 5,878,775 | A |   | 3/1999  | Tamburro, Jr. |
| 7,365,832 | B2|   | 4/2008  | Kase |
| 8,035,515 | B2|   | 10/2011 | Jang et al. |
| 8,279,417 | B2|   | 10/2012 | Hocknell et al. |
| 2008/0265595 | A1 | | 10/2008 | Perlman |
| 2010/0024916 | A1 | | 2/2010  | Dyer |

(Continued)

FOREIGN PATENT DOCUMENTS

| CA | 2623601 A1 | * | 6/2008  | .............. A01M 1/02 |
| CN | 206994133 U | * | 2/2018 | |
| GB | 2550495 A  | * | 11/2017 | ........... A01K 63/045 |

OTHER PUBLICATIONS

Vacuum Pump, Wikipedia, Available Online at: https://en.wikipedia.org/wiki/Vacuum_pump, Retrieved from Internet on Dec. 17, 2018, pp. 1-5.

*Primary Examiner* — Joseph C Rodriguez

(74) *Attorney, Agent, or Firm* — Kilpatrick Townsend & Stockton LLP

(57) ABSTRACT

Devices, systems, and methods for transporting or transferring insect pupae in an aqueous solution are described. The system includes a tank containing a solution with insect pupae, a transfer chamber having an outlet at a bottom portion of the chamber, a solution inlet, an evacuation channel, and a depth measurement system. A tube fluidly connects to tank and the transfer chamber. An evacuation device connected to the evacuation channel removes air from the transfer chamber and generates a vacuum therein to draw the solution through the tube into the transfer chamber.

7 Claims, 4 Drawing Sheets

(56) References Cited

U.S. PATENT DOCUMENTS

Figure 1:
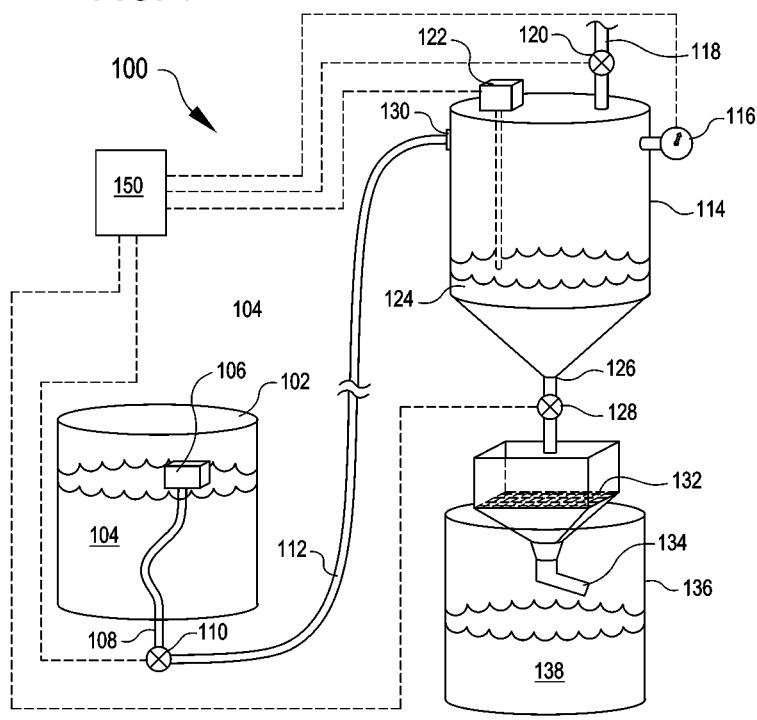

| | | | |
|---|---|---|---|
| 2012/0138524 A1* | 6/2012 | Koishi | C02F 1/004 |
| | | | 210/263 |
| 2015/0176260 A1 | 6/2015 | Ball et al. | |
| 2018/0080206 A1 | 3/2018 | Le | |
| 2018/0092339 A1 | 4/2018 | Massaro et al. | |
| 2018/0271072 A1 | 9/2018 | Sobecki et al. | |
| 2021/0008600 A1* | 1/2021 | Greeley | B07C 5/36 |
| 2022/0053743 A1* | 2/2022 | Lepek | B07B 1/22 |

\* cited by examiner

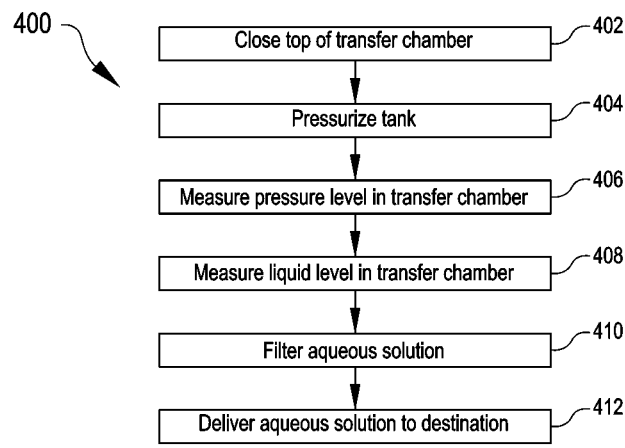
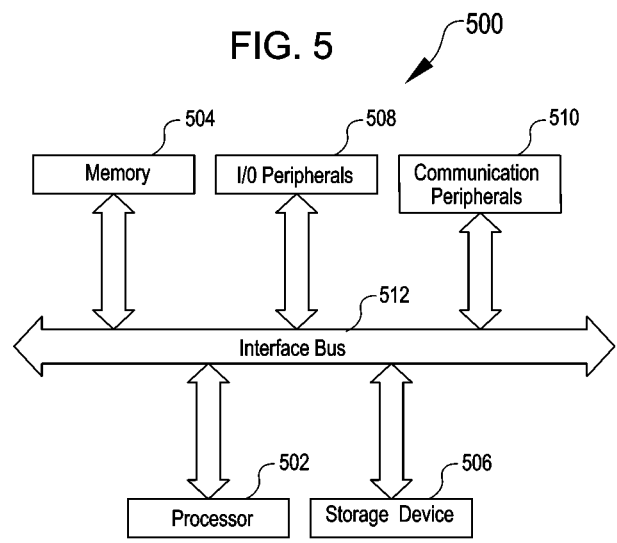

PUPAE TRANSFER DEVICE

CROSS-REFERENCE TO RELATED APPLICATIONS

This application claims priority to U.S. Provisional Patent Application No. 62/877,973 filed on Jul. 24, 2019, titled "Pupae Vacuum Transportation Device," the contents of which are hereby incorporated by reference in their entirety.

BACKGROUND

Many Sterile Insect Technique (SIT) programs require processing insects and moving insects in various stages of development. Typically, transfer processes involve moving trays or containers between locations within the process. Many other methods involve transferring insects using gravity feeds. During some transfer processes, insects may escape or be damaged while moving between locations.

SUMMARY

One general aspect includes an insect pupae transfer system, including a holding tank to hold a solution including insect pupae and a transfer chamber. The transfer chamber includes a liquid outlet at a bottom and a liquid inlet positioned above the bottom of the transfer chamber. The insect pupae transfer system also includes an air passage providing a conduit between an inside of the transfer chamber and an exterior of the transfer chamber and a depth measurement system to output a liquid depth within the transfer chamber. A delivery tube couples to the liquid inlet and the holding tank. The insect pupae transfer system also includes an evacuation device connected to the air passage to reduce an air pressure within the transfer chamber by removing air from the transfer chamber to cause at least a portion of the solution including the insect pupae to move, via the delivery tube, from the holding tank to the transfer chamber.

Implementations may include one or more of the following features. The delivery tube extending into the holding tank and coupling to a float to maintain an end of the portion of the delivery tube near a surface of a liquid within the holding tank. The evacuation device includes a Venturi pump or a vacuum pump. The insect pupae transfer system where the liquid outlet includes a valve. The depth measurement system is at least one of an optical sensor, an acoustic sensor, a conductive sensor, a flotation sensor, or a weight sensor. The insect pupae transfer system may further include a computing device including a non-transitory computer-readable medium and a processor, the processor configured to execute processor-executable instructions stored in the non-transitory computer-readable medium to transmit a first signal to cause a valve of the liquid outlet to close, transmit a second signal to cause the evacuation device to remove air from the transfer chamber, determine the liquid depth in the transfer chamber based at least in part on the liquid depth from the depth measurement system, and upon determining that the liquid depth meets or exceeds a predetermined depth, transmit a third signal to cause the valve of the liquid outlet to open. The insect pupae transfer system further including a filter positioned downstream of the liquid outlet. Implementations of the described techniques may include hardware, a method or process, or computer software on a computer-accessible medium.

Another general aspect includes a method of transporting insect pupae, including depositing an aqueous solution into a holding tank, the aqueous solution including insect pupae, the holding tank in fluid communication with a transfer chamber using a delivery tube. The method includes closing an outlet of the transfer chamber and reducing an air pressure in the transfer chamber by removing air from the transfer chamber using an evacuation device. The method of transporting insect pupae also includes drawing, via the reduced air pressure, a portion of the aqueous solution including the insect pupae from the holding tank into the transfer chamber through the delivery tube. The method of transporting insect pupae further includes determining a liquid depth within the transfer chamber, and in response to receiving a signal from a fluid sensor indicating a quantity of aqueous solution in the holding tank meets or exceeds a predetermined depth, deactivating the evacuation device. Other embodiments of this aspect include corresponding computer systems, apparatus, and computer programs recorded on one or more computer storage devices, each configured to perform the actions of the methods.

Implementations may include one or more of the following features. The method further includes opening the outlet of the transfer chamber in response to the signal from the fluid sensor indicating the quantity of aqueous solution in the holding tank meets or exceeds the predetermined depth to dispense the portion of the aqueous solution including the insect pupae from the transfer chamber. The method also further includes filtering the aqueous solution downstream of the outlet of the transfer chamber. The method where removing the air from the transfer chamber includes removing the air with a Venturi pump or a vacuum pump. The method where the delivery tube includes a portion disposed within the holding tank, and further including coupling the portion of the delivery tube to a float within the holding tank to maintain an end of the portion of the delivery tube at or near an upper surface of liquid within the holding tank. The method where determining the liquid depth within the transfer chamber includes measuring with at least one of an optical sensor, an acoustic sensor, a conductive sensor, a flotation sensor, or a weight sensor. The method where the outlet includes a valve. Implementations of the described techniques may include hardware, a method or process, or computer software on a computer-accessible medium.

Another general aspect includes a system for transporting insect pupae, including a holding tank having a sealable opening and a fluid outlet, the holding tank containing an aqueous solution including insect pupae. The system also includes a delivery tube fluidly coupled to the holding tank, a valve coupled to the delivery tube to close the fluid outlet of the holding tank, and a pressure system fluidly coupled to the holding tank. The system also includes a pressure monitoring system fluidly coupled with the holding tank that measures a pressure level in the holding tank; and one or more processors configured to cause the valve to alternately open and close the fluid outlet as well as cause the pressure system to increase an air pressure level in the holding tank to drive the aqueous solution through the delivery tube to a destination. The system also receives a signal from the pressure monitoring system based on the air pressure level.

Implementations may include one or more of the following features. The system further including a detection system to detect when the aqueous solution exits the delivery tube. The detection system may include an optical sensor or a conductive sensor. The pressure system is configured to maintain the pressure level in the holding tank while the detection system detects the aqueous solution is exiting the delivery tube. The delivery tube may include a float at a first end of the delivery tube to maintain the first end of the delivery tube below a surface of the aqueous solution in the holding tank. The system further including a filter at a second end of the delivery tube. The system further including a liquid level detection system to detect an level of the aqueous solution in the holding tank and convey a signal corresponding to the level of the aqueous solution to the one or more processors.

Yet another general aspect includes a method for transporting insect pupae, including providing a holding tank having a sealable opening and an outlet that contains an aqueous solution of insect pupae. The method also includes providing a delivery tube fluidly coupling the holding tank and a container at a destination. The holding tank is sealed at the sealable opening and the pressure level in the holding tank is increased with a pressure system to drive the aqueous solution from the holding tank through the delivery tube. The method also includes after increasing the pressure level in the holding tank, detecting when the aqueous solution exits the delivery tube at the destination. The method also includes maintaining the pressure level in the holding tank at a constant pressure while the aqueous solution exits the delivery tube to transfer the aqueous solution from the holding tank to the container. Other embodiments of this aspect include corresponding computer systems, apparatus, and computer programs recorded on one or more computer storage devices, each configured to perform the actions of the methods.

Implementations may include one or more of the following features. The method further including determining a depth of the aqueous solution in the holding tank and ceasing to increase the pressure level when the depth in the holding tank reaches a predetermined level. The end of the delivery tube includes a float to maintain the end below an upper surface of the aqueous solution within the holding tank. The method further including filtering the aqueous solution downstream of the delivery tube. The method where detecting when the aqueous solution exits the delivery tube includes detecting using an optical detection system. Implementations of the described techniques may include hardware, a method or process, or computer software on a computer-accessible medium.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 1 illustrates a system for transferring insect pupae, according to at least one example.

FIG. 2 illustrates an example process for transferring insect pupae, according to at least one example.

FIG. 3 illustrates a system for transferring insect pupae, according to at least one example.

FIG. 4 illustrates a process for transferring insect pupae, according to at least one example.

FIG. 5 illustrates a computer system for use with processes and systems described herein, according to at least one example.

FIG. 6 illustrates a system for transferring insect pupae, according to at least one example.

FIG. 7 illustrates a process for transferring insect pupae, according to at least one example.

DETAILED DESCRIPTION

Examples are described herein in the context of insect transfer and movement, especially at the pupal or larval stage. Those of ordinary skill in the art will realize that the following description is illustrative only and is not intended to be in any way limiting. For example, transport systems and techniques described herein can be used with a variety of insect processing and techniques. Examples described herein relate to transporting insects, specifically mosquitoes in the pupa stage, though techniques described herein can be used to transport other insects or mosquitoes in other stages, such as a larval stage. Therefore, throughout the description, references to a pupal stage may also include larval stages or other stages. Reference will now be made in detail to implementations of examples as illustrated in the accompanying drawings. The same or similar reference indicators will be used throughout the drawings and the following description to refer to the same or similar items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Current methods of transporting insect pupae typically involve loading the pupae, suspended in water, into trays or containers, which may include tops open to the air or covered with a lid. The trays or containers can then be moved by hand or by automated equipment. Moving the trays or containers, whether by hand or by automated equipment, may risk spills, releases, or damage to the insects. Not to mention, in many conventional cases where trays are transferred one at a time, the speed at which trays of insect pupae may be moved is quite slow and inefficient because of the need to prevent spilling while transporting. In a rearing stage of a SIT program, the insect pupae are moved quite frequently. For example, the insect pupae may be transported between different stations in a facility for continuous processing, including rearing, feeding, storage, imaging, and sorting. Additionally, moving insect pupae through pumps or other systems involving moving parts may cause damage to insect pupae when they come into contact with moving components of pumps or other such devices.

The devices, systems, and methods described herein provide a fast and efficient method for securely and safely transporting insect pupae. The insects are transported while suspended in an aqueous solution. Because of this, the pupae can be carried in the aqueous solution between stations in a facility such as from a rearing station to a sorting station. The described devices, systems, and methods, which transport insects in the pupal stage, are able to do so with large quantities of insects at a higher throughput and or less effort and potential damage to insects than with adult insects. For some processes, insects must be moved both vertically and horizontally and may not be transported only through gravitational means. Additionally, it is important in SIT programs to transport insects in a secure manner to prevent insect releases and in a safe manner to transport the insects without damage.

In an illustrative example, an insect pupae transfer system includes a holding tank, a transfer chamber, and a delivery device for directing the insect pupae to their final destination. The transfer chamber is used to provide an intermediate location for staging and transferring insect pupae in solution between the holding tank and a destination, such as a vat or other container. The transfer chamber includes an evacuation device such as a vacuum pump for removing air or generating a vacuum within the transfer chamber. The transfer chamber also includes a fluid inlet and a fluid outlet. The inlet is located above the bottom of the transfer chamber and the outlet is located at a bottom or bottom-most portion of the transfer chamber. A delivery tube couples an opening of the transfer chamber and the holding tank. The system may be controlled by a human operator, or may be computer controlled, with a computing device sending and receiving signals to control and monitor various operations of the system including valve opening and closing and depth or pressure measurements. In operation, when the evacuation device generates a vacuum within the transfer chamber, the solution containing insect pupae is drawn through the delivery tube, by the vacuum, into the transfer chamber. When the outlet of the transfer chamber is opened, the vacuum generated within the transfer chamber is lost and the solution containing insect pupae within the transfer chamber flow freely through the fluid outlet. For example, the solution containing the insect pupae can flow out of the fluid outlet and into a delivery device positioned near the fluid outlet which directs the pupae to their destination and may include a movable armature or movable portion to optionally direct the pupae into alternating destinations. The transfer chamber may also include a depth measurement system for determining a depth of liquid within the transfer chamber. The fluid outlet may be opened based at least in part on the liquid depth from the depth measurement system indicating a predetermined height or volume of liquid is contained within the transfer chamber.

The systems and methods described herein allow and provide a means for transporting insect pupae in a secure manner between two locations. The use of the vacuum to draw the pupae and aqueous solution through the delivery tube allows the transport system to be path-independent and rely partially on gravity. In other words, the transport systems herein enable insect pupae transfer to locations higher than an initial staging area, or to traverse or overpass equipment or devices in a rearing facility. With the holding tank, the insect pupae are drawn, through a secure and enclosed tube, to an intermediate stage, from which point the insect pupae may transfer solely based on gravity. The enclosed delivery tube and fully enclosed transfer system ensures that no insect pupae may be prematurely released or lost, and monitoring systems described herein ensure that the insect pupae are not damaged during transfer. This illustrative example is given to introduce the reader to the general subject matter discussed herein and the disclosure is not limited to this example. The following sections describe additional non-limiting examples and techniques relating to using an insect pupa transfer system for transporting or re-locating insect pupae.

Turning now to the figures, FIG. 1 illustrates insect pupae transfer system 100 for transferring insect pupae in solution from a first location (e.g., holding tank 102) to a second location (e.g., container 136), according to at least one example. In particular, insect pupae transfer system 100 includes holding tank 102, container 136, transfer chamber 114, and delivery tube 112. Holding tank 102 may be any container suitable for holding solution 104 containing insect pupae. In some examples, holding tank 102 may be a rearing tank, a hatching tank, or other tank used in production of mosquitoes or insects for SIT programs. Holding tank 102 includes outlet 108 and valve 110 where delivery tube 112 exits holding tank 102. Outlet 108 is positioned at a bottom or lower portion of holding tank 102. When solution 104 is drawn out of holding tank 102, the level of solution 104 in holding tank 102 drops and therefore outlet 108, when positioned at the bottom of holding tank 102, may make it easier to remove a higher portion or amount of solution 104 from holding tank 102.

Valve 110, as well as other valves described herein may be actuated manually or electronically. In some examples, valve 110 and other valves may be an angle valve, back pressure valve, ball valve, block valve, bevel gear operated valve, crown valve, butterfly valve, safety valve, globe valve, gate valve, wing valve, plug valve, standing valve, or any other suitable valve. Valve 110, and other valves described herein may include an actuator or other electromechanical device such as a servo to actuate opening and closing of the valve upon receiving a signal from a computer device.

Functionality described herein may be performed using computing device 150. For example, computing device 150 may communicate with valve 120, valve 110, valve 128, pressure monitoring system 116, and depth measurement system 122, e.g., to actuate the valves or obtain sensor readings. Such communication may be wired or wireless. Further, they may be carried out over a network such as the internet or a local network. Computing device 150 is described in further detail with respect to FIG. 5 below.

In some examples, outlet 108 may be positioned at locations other than the bottom of holding tank 102. For example, outlet 108 may be positioned on the side of holding tank 102. As illustrated, delivery tube 112 has a portion positioned within holding tank 102 with float 106 at or near the end of delivery tube 112, e.g., by coupling to one side of the outlet 108. It should be appreciated that the delivery tube 112 may include multiple discrete tubes that are connected to various components to provide a fluid path from the holding tank 102 to the transfer chamber 114. For example, a first portion of delivery tube 112 may be within holding tank 102 connecting to outlet 108, with a second portion of delivery tube extending from outlet 108 to the transfer chamber 114. Float 106 may be configured to maintain the end of delivery tube 112 at or near the surface of solution 104. Many insect pupae float at or near the upper surface of the water, so drawing solution 104 from the region at or near the surface of solution 104 may move insect pupae out of holding tank 102 quickly or more efficiently than drawing solution 104 from a region near outlet 108 at the bottom of holding tank 102 or at other locations within holding tank 102.

Delivery tube 112 connects to transfer chamber 114 at inlet 130, where solution 104 with insect pupae is drawn into transfer chamber 114. Transfer chamber 114 also includes outlet 126 and valve 128 in addition to pressure monitoring system 116, valve 120, evacuation tube 118, and depth measurement system 122. Inlet 130 is shown near an upper portion of transfer chamber 114, though, in some examples, it may be positioned anywhere on transfer chamber 114. For example, inlet 130 may be near a bottom or middle portion of transfer chamber 114. Positioning inlet 130 lower on a side wall or near a bottom of transfer chamber 114 may result in insect pupae entering through inlet 130 without dropping into solution 124. Dropping a significant vertical distance may result in damage to insect pupae and therefore reducing the amount vertical drop may help reduce or prevent damage to insect pupae during transfer.

In some examples, detection system 140, such as an optical sensor or a conductive sensor, may detect when solution 104 exits delivery tube 112 into transfer chamber 114. The system may be configured to maintain a pressure level within transfer chamber 114 at a pressure where solution 104 exits delivery tube 112 without further increasing the pressure differential. For example, once detection system 140 detects solution 104 exiting the delivery tube 112, the pressure within transfer chamber 114 is maintained to keep a pressure differential between the surrounding environment and inside transfer chamber 114 substantially constant such that the flow of solution 104 through delivery tube 112 is at a substantially constant flow rate, driven by the maintained pressure differential. As solution 104 exits delivery tube 112 into transfer chamber 114, the pressure level within transfer chamber 114 will increase (due to the addition of fluid volume and corresponding reduction in gas volume), therefore additional air may be removed from transfer chamber 114 as described below. This may allow system 100 to expose insect pupae to the least pressure differential necessary while still transporting them through system 100. Finally, outlet 126 and valve 128 are positioned at the bottom of transfer chamber 114 to allow solution 124 to drain from transfer chamber 114 by gravity when valve 128 is opened.

Transfer chamber 114 includes pressure monitoring system 116 for detecting and determining a pressure level within transfer chamber 114. Pressure monitoring system 116 may include any type of conventional pressure gauges or electronic pressure measuring systems designed to measure the gauge pressure of transfer chamber 114, especially detecting pressures lower than the surrounding atmospheric pressure. The detection system 140 may detect the solution 104 exiting the delivery tube 112 and the pressure monitoring system 116 may then be used in connection with the evacuation device 142 described below to maintain the pressure level within the transfer chamber 114 while transferring insect pupae. The pressure monitoring system 116 may be incorporated in addition to the detection system 140, or in some examples, the pressure monitoring system 116 alone may be used to monitor a pressure level within the transfer chamber 114 and maintain it at or below a critical level.

Pressure monitoring system 116 may be connected, either directly or indirectly to a regulation system or computer device 150 that prevents the pressure differential between the inside of transfer chamber 114 and surrounding air pressure from becoming too large. With large pressure differences, either above or below surrounding air pressure, the insect pupae may become damaged by the fluctuations in pressure. For instance, high pressures may crush or compress insect pupae and result in damage or loss in insect pupae while transporting. On the other hand, pressures that are too low may likewise damage the insect pupae during transport, for example causing the pupae to experience too great of a vacuum may rupture portions of the insect pupae body. Accordingly, the pressure range may be between 0 PSI and 20 PSI. In some examples, the pressure range may be between 4 PSI and 20 PSI. In some further examples, the pressure range may be between 7 PSI and 21 PSI. In some examples, the pressure range is less than 14 PSI for the system 100 of FIG. 1 involving pressures lower than atmospheric pressure or greater than 14 PSI for the system 300 of FIG. 3.

Evacuation tube 118 and valve 120 are connected to transfer chamber 114 to remove air from transfer chamber 114. Air may be removed from transfer chamber 114 through evacuation tube 118 which may be connected to evacuation device 142 such as a vacuum pump, vacuum chamber, Venturi pump, or other vacuum. In any case, evacuation tube 118 is used to pump or remove air from the transfer chamber 114. Valve 120 may be operated to intermittently remove air from transfer chamber 114. For example, when evacuation tube 118 is connected to a volume of lower pressure than in the transfer chamber 114, such as a vacuum or low pressure volume contained within a vacuum chamber, valve 120 may be opened intermittently to remove air and thereby reduce the pressure within transfer chamber 114. As described above, valve 120 or the evacuation device 142 may be controlled to maintain a pressure level within transfer chamber 114 within the ranges described herein.

In some examples, the evacuation device may be a vacuum pump, while in some other examples, the evacuation device may include a vacuum source or Venturi pump or any other device capable of evacuating air from the transfer chamber and generating a vacuum. With a vacuum pump, air is actively pumped out of evacuation tube 118. A Venturi pump relies on the Venturi principle, whereby a fluid flow through a constricting nozzle creates an area of low pressure at the expansion side of the nozzle. Evacuation tube 118 may be connected to a Venturi vacuum generator at the low pressure location at the expansion side of the nozzle, thereby pulling air molecules into the flow through the Venturi vacuum generator. The fluid outlet of the transfer chamber may include a delivery device to direct the solution into one or more vats, tanks, or other such destinations from the transfer chamber. In some examples, the delivery device may include a tube, while in some other examples it may include an automated arm and delivery conduit for changing a location and orientation of the delivery conduit to deliver into different tanks or destinations. The fluid outlet may also include a sieve or filter for filtering or sorting foreign or undesired matter out of the solution. In some examples, the delivery tube 112 may include a float or other device to maintain an inlet of the delivery at, below, or near a surface of the solution within the holding tank 102.

Depth measurement system 122 may include any number of mechanical, optical, conductive, weight-based, or other systems to measure or determine a depth or volume of solution 124 within transfer chamber 114. In some examples, depth measurement system 122 may include an optical sensor which detects or reflects a light or other emission which may also be emitted by depth measurement system 122. In some examples, depth measurement system 122 may include a float which floats at the surface of solution 124 and outputs an indication of the height of solution 124 within transfer chamber 114. In some examples, one or more conductive sensors may complete a circuit when in contact with solution 124 and based on a height of the completed circuit, may output a height of solution 124. A weight displacement system may sense a weight of transfer chamber 114 as solution 124 flows into transfer chamber 114, thereby increasing the weight. The system may output a weight, volume, or a height of solution 124 determined based on the weight of transfer chamber 114 and solution 124, and other properties of transfer chamber 114 such as interior volume.

Once the depth measurement system 122 determines the depth or volume of solution 124 within transfer chamber 114 is at a level that matches a predetermined height or volume, the system may be controlled to open valve 128 and allow solution 124 to flow through outlet 126. The predetermined height may be selected based on any number of factors such as a percentage of transfer chamber 114 volume being occupied, a volume at which the pressure within transfer chamber 114 nears a maximum pressure difference, or other factors.

In some examples, valve 128 may be opened after a set period of operating time. For example, valve 128 may be set to open automatically after 30 seconds of operation, thereby emptying transfer chamber 114 of solution 124 and, upon closing valve 128, beginning to draw solution 104 into transfer chamber 114 again.

Downstream of outlet 126 and valve 128 is sieve 132 which may filter out or catch insect pupae of a certain size or foreign or unwanted matter. In some examples, a mesh of sieve 132 may be sized to allow male insect pupae to pass through while catching or preventing passage of larger, such as female, insect pupae. For example, male mosquito pupae may have a diameter or maximum dimension of 1 mm to 2 mm and female mosquito pupae may be larger than the male pupae, so a mesh size which is sized at or near the size of the male mosquito pupae will allow male pupae to advance and proceed through sieve 132 while everything else would be captured at sieve 132 for removal or sorting. In some examples, the sieve 132 may catch all pupae, male and female.

Sieve 132 may be located upstream of distribution device 134 for distributing solution 124 into container 136, or into other tanks, containers, systems, or locations. Container 136 may contain solution 138 to provide a liquid environment into which insect pupae may be deposited after passing through sieve 132. Distribution device 134 may include a telescoping or extending arm or a redirection device to move an outlet of distribution device 134 to an additional container (not shown) or other location to deliver solution 124 and insect pupae to varying final locations. In other examples, sieve 132 may be positioned downstream of distribution device 134.

In operation, holding tank 102 initially contains solution 104 including water and insect pupae. Holding tank 102 is connected to delivery tube 112 at valve 110 which is open during transfer of insect pupae. Solution 104 is drawn into delivery tube 112 due to the pressure differential between holding tank 102, the surrounding environment, and transfer chamber 114 created by evacuating transfer chamber 114 as described herein. The greater the pressure differential results in an increased flow rate of solution 104 into transfer chamber 114. Alternatively, a larger pressure differential allows a solution 104 to traverse a greater height differential from holding tank 102 to transfer chamber 114.

One benefit of insect pupae transfer system 100 as described herein is that the route traversed by delivery tube 112 is nearly entirely path-independent. For instance, delivery tube 112 may wind through or around other machinery or devices within a production facility in curved paths which undulate and vary in height and position. Traversing such complex environments is difficult with traditional transfer systems such as belt systems because turns, dips, and obstacles present significant challenges to overcome. Because delivery tube 112 may be flexible and because fluid is pulled by low-pressure, delivery tube 112 may follow any path from holding tank 102 to transfer chamber 114. The path-independence of insect pupae transfer system 100 is only limited by the pressure limits described herein, however, in the absence of pressure restrictions to avoid damage to one particular type of insect, for example when transporting other materials or types of pupae that are more resistant to pressure changes, the path of delivery tube 112 is not limited by a pressure range and may therefore have greater vertical displacement along the path.

Figure 2:
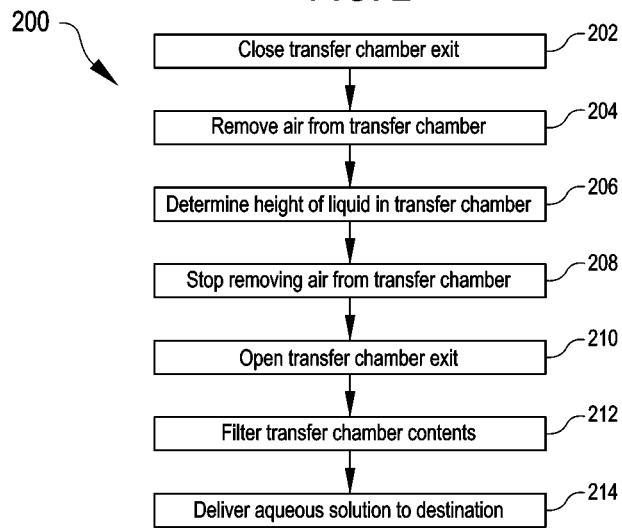

FIGS. 2 and 4 illustrate example flow diagrams showing processes 200, 400, according to examples of pupae vacuum transport. These processes are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

FIG. 2 illustrates process 200 for transporting insect pupae, according to at least one example and will be described with respect to the system 100 shown in FIG. 1. Process 200 for transporting insect pupae may be implemented by computer device 150 as described above. In some examples, process 200 and any other process described herein may be performed, at least in part, by a human operator. In process 200, at block 202, computer device 150 sends a signal to valve 128 at outlet 126 of transfer chamber 114 to close and thereby shut transfer chamber 114 off to the environment. In this example, the only other openings into transfer chamber 114 are inlet 130 where solution 104 will flow from delivery tube 112 and valve 120 where evacuation tube 118 and evacuation device 142 are connected.

At block 204, evacuation device 142 removes air from transfer chamber 114 through evacuation tube 118. For example, computing device 150 may send a signal to evacuation device 142 to begin removing the air from transfer chamber 114. In some examples, a human operators may actuate evacuation device 142 to begin removing the air. Evacuation device 142 may remove air at a uniform rate or at any suitable rate. This air may be removed through a vacuum pump, Venturi pump, vacuum chamber, or other such device.

Once at least some portion of air is removed from transfer chamber 114, the pressure inside transfer chamber 114 will be lower than the surrounding air pressure, including the pressure experienced by solution 104 at holding tank 102. This pressure differential, described above, drives solution 104 through delivery tube 112 into transfer chamber 114.

At block 206, depth measurement system 122 determines the height or volume of solution 104 contained within transfer chamber 114. In some examples, the depth or volume may be continuously measured or monitored or in some instances, depth measurement system 122 may only detect when the level of solution 104 within transfer chamber 114 reaches a predetermined height. In at least one example, electrical leads may be set at the predetermined height within transfer chamber 114 such that when solution 104 reaches the predetermined height, solution 104 will contact each of the leads and complete an electrical circuit, causing a signal to be produced. The signal may notify a manual operator that transfer chamber 114, or a valve connected thereto, should be opened, or the signal itself may be sent to computer device 150 which will carry on additional procedures.

At block 208, computer device 150 may receive the signal from the depth measurement system 122 indicating the height of solution 124 and when the height of the solution reaches a predetermined threshold, computer device 150 may send a signal to close valve 120 or shut off evacuation device 142 to stop removing air from transfer chamber 114. Shutting off evacuation device 142 or closing valve 120 will slow and eventually stop the flow of solution 104 through delivery tube 112 because the pressure differential will no longer be sufficient to draw solution 104 into delivery tube 112 and into transfer chamber 114.

At block 210, the outlet 126 of transfer chamber 114 is opened. The process of block 204, drawing insect pupae through delivery tube 112, may be performed simultaneously with block 210 in some instances, or may be completed previously to performing the process of block 210. In some examples, this is performed by computer device 150 instructing valve 128 to open, allowing solution 124 and the insect pupae contained therein to flow through outlet 126. This may be followed by, at block 212, filtering the contents of transfer chamber 114. In some examples, including as described above, a filter or sieve 132 filters the contents after they exit outlet 126. For example, filtering the contents of transfer chamber 114 may include directing solution 124 from the outlet 126 into sieve 132. Such filtering may be performed to sort out different sizes of insect pupae or remove foreign or unwanted matter from solution 124. At block 214 of the process 200, the solution 124 is delivered to a destination. As described herein, distribution device 134 delivers solution 124 is directed to a final destination, container 136. Block 214 may include diverting or moving a distribution device 134 to deliver solution 124 to a different container or destination as desired. In some examples, delivering solution 124 to the destination includes relying on gravity or downward sloping to deliver to the destination.

Figure 3:
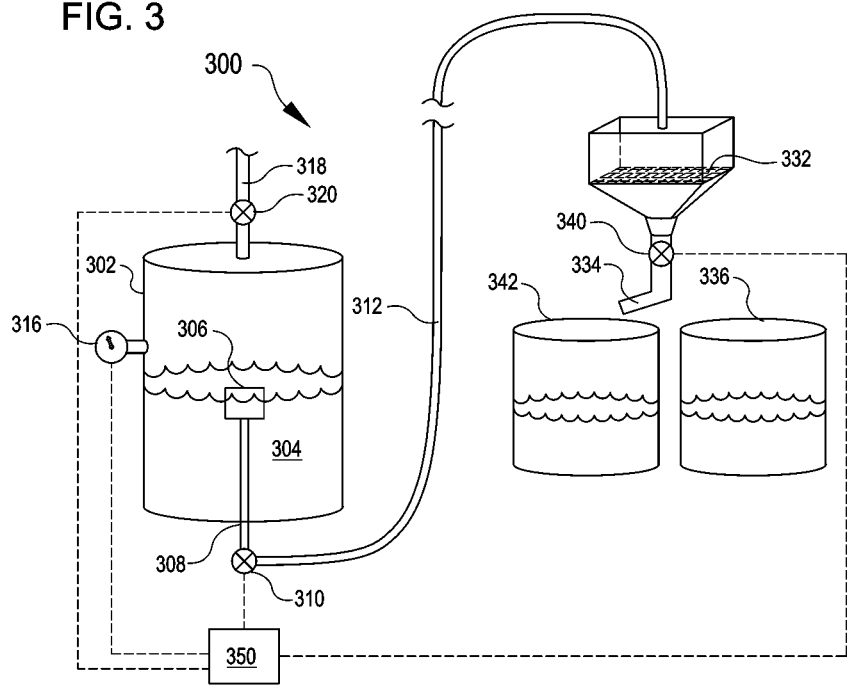

FIG. 3 illustrates insect pupae transfer system 300 for transferring insect pupae in solution from a first location or holding tank 302 to a second location or container 336 or third container 342, according to at least one example. The example shown in FIG. 3 relies on a positive pressure rather than an evacuation device to provide force to transfer insect pupae in solution from the holding tank 302 to another container. In particular, insect pupae transfer system 300 includes holding tank 302, containers 336 and 342, and delivery tube 312. Holding tank 302 is an example of holding tank 102 described previously above. Holding tank 302 includes outlet 308 and valve 310 where delivery tube 312 exits holding tank 302. Outlet 308 is positioned at a bottom or lower portion of holding tank 302. When solution 304 is drawn out of holding tank 302, the level of solution 304 in holding tank 302 drops and therefore outlet 308, when positioned at the bottom of holding tank 302, may make it easier to remove all or substantially all of solution 304 from holding tank 302. In some examples, outlet 308 may be positioned above the bottom of holding tank 302 to allow pupae, which float, to flow out through outlet 308 without emptying the whole holding tank 302.

Functionality described herein may be performed using computing device 350. For example, computing device 350 may send signals to control valve 310, valve 340, valve 320, and communicate with pressure monitoring system 316. Such communication may be wired or may be carried out over a network such as the internet or a local network. Computing device 350 is described in further detail with respect to FIG. 5 below.

In some examples, outlet 308 may be positioned at locations other than the bottom of holding tank 302. For example, outlet 308 may be positioned on the side or the top of holding tank 302. Delivery tube 312 may extend into holding tank 302 with float 306 at or near the end of delivery tube 312. Float 306 may be configured to maintain the end of delivery tube 312 at or near the surface of solution 304. Many insect pupae float at or near the upper surface of the water, so drawing solution 304 from the region at or near the surface of solution 304 may move insect pupae out of holding tank 302 quickly or more efficiently than drawing solution 304 from a region near outlet 308 at the bottom of holding tank 302.

Holding tank 302 includes pressure monitoring system 316 for detecting and determining a pressure level within holding tank 302. Pressure monitoring system 316 may include any type of conventional pressure gauges or electronic pressure measuring systems designed to measure the gauge pressure of holding tank 302, especially detecting pressures greater than the surrounding atmospheric pressure. Pressure monitoring system 316 may be connected, either directly or indirectly to a regulation system or computer device 350 that prevents the pressure difference between the inside of holding tank 302 and surrounding air pressure from becoming too large. With large pressure differences, either above or below surrounding air pressure, the insect pupae may become damaged by the fluctuations in pressure. For instance, high pressures may crush or compress insect pupae and result in damage or loss in insect pupae while transporting. On the other hand, pressures that are too low may likewise damage the insect pupae during transport. Accordingly, in at least one example the pressure range is limited to 7 PSI above or below atmospheric pressure. For example, the pressure range may be limited to between 1 PSI and 20 PSI. In some examples, the pressure range may extend above this range to include pressures up to 36 PSI and higher—provided the pupae can withstand the pressure.

Holding tank 302 includes air inlet 318 and valve 320 connected to selectively deliver air into holding tank 302 to increase the pressure within holding tank 302. Valve 320 may be operated to intermittently introduce air into holding tank 302 from compressor 344. Compressor 344 may be a high pressure source such as a tank containing compressed fluid or other such source of pressurized fluid. As described above, valve 320 or compressor 244 may be controlled to maintain a pressure level within holding tank 302 within the ranges described herein. The flow through delivery tube 312 may be maintained at a constant rate by monitoring the pressure level within holding tank 302 and adjusting valve 320 to maintain a constant pressure within holding tank 302 as solution 304 flows out through delivery tube 312.

Holding tank 302 may include a depth measurement system as described above to measure or determine a depth or volume of solution 304 within holding tank 302. This system may be used to automatically shut off system 300 when solution 304 reaches a predetermined height such as half the height of holding tank 302 or when holding tank 302 is nearly empty.

Downstream of delivery tube 312 is sieve 332 which may filter out or catch insect pupae of a certain size or foreign or unwanted matter. In some examples, a mesh of sieve 332 may be sized to allow male insect pupae to pass through while catching or preventing passage of larger, such as female, insect pupae. For example, male mosquito pupae may have a diameter or maximum dimension of 1 mm to 2 mm and female mosquito pupae may be larger than the male pupae, so a mesh size which is sized at or near the size of the male mosquito pupae will allow male pupae to advance and proceed through sieve 332 while everything else would be captured at sieve 332 for removal or sorting.

Sieve 332 may be located upstream of a distribution device 334 for distributing solution 304 into container 336, third container 342, or into other tanks, containers, systems, or locations. Container 336 may contain a solution to provide a liquid environment into which insect pupae may be deposited after passing through sieve 332. Distribution device 334 may include a telescoping or extending arm or a redirection device, such as a channel which can be moved above a series of containers, to move an outlet of distribution device 334 to an additional container (not shown) or other location to deliver solution 304 and insect pupae to varying final locations.

In operation, holding tank 302 initially contains solution 304 including water and insect pupae. Holding tank 302 is connected to delivery tube 312 and valve 310 is open during transfer of insect pupae. Solution 304 is pushed into delivery tube 312 due to the high pressure zone created in holding tank 302. The high pressure zone may have a greater pressure differential when compared with the surrounding air pressure to increase a flow rate of solution 304 into delivery tube 312 or to traverse a greater height differential from holding tank 302 an exit of delivery tube 312.

One benefit of the insect pupae transfer system 300 described herein is that the route traversed by delivery tube 312 is nearly entirely path-independent and may be limited only by the weight of water and hydrostatic pressure. For instance, delivery tube 312 may wind through or around other machinery or devices within a production facility in curved paths which undulate and vary in height and position. Traversing such complex environments is difficult with traditional transfer systems such as belt systems because turns, dips, and obstacles present significant challenges to overcome. In the present case, delivery tube 312 may be flexible and may therefore follow any path from holding tank 302 to the exit of delivery tube 312. The path-independence of system 300 is only limited by the pressure limits described herein, however, in the absence of pressure restrictions to avoid damage to one particular type of insect, for example when transporting other materials or types of pupae that are more resistant to pressure changes, the path of delivery tube 312 is not limited by a pressure range and may therefore have greater vertical displacement along the path.

FIG. 4 illustrates example process 400 for transporting insect pupae, according to at least one example. Process 400 for transporting insect pupae may be implemented by a computer device 350 as described above. In some examples the processes may also be performed by a human operator. At block 402 the holding tank 302 is closed and sealed. The seal must be able to support an increase in air pressure within holding tank 302. In some instances, the holding tank may be closed by an operator placing a lid over the holding tank 302.

At block 404, holding tank 302 is pressurized. To pressurize holding tank 302, computer device 350 instructs valve 320 to open, pumping air or another fluid to into holding tank 302 through air inlet 318, thereby increasing the pressure within holding tank 302. In some examples, an operator may open valve 320 to allow fluid to flow into holding tank 302 thereby increasing the pressure. At block 406, pressure monitoring system 316 measures the pressure level within holding tank 302. This pressure level may be monitored and used to control valve 320 or valve 310 to maintain pressure within holding tank 302 without increasing the pressure beyond a threshold at which the insect pupae may be damaged as described above. For example, when a pressure level within holding tank 302 decreases, an operator may open valve 320 to introduce additional fluid and increase the pressure level. Valve 320 may also be closed to allow the pressure in holding tank 302 to reduce as solution 304 flows out of holding tank 302, conversely, the pressure may be increased by opening valve 320 and introducing additional fluid.

Block 408 includes measuring a liquid level within holding tank 302. A depth measurement system, similar to that described with respect to FIG. 1, may be used to measure the liquid level within the holding tank. The liquid level may be measured and cause a signal to be relayed when the liquid level reaches a predetermined level, such as near empty, at which point the system may power down to stop the transfer process. In some examples, the liquid level is reported to a computing device 150. The computing device 150 may carry out other processes, such as those described herein, with the liquid level. For example, the computing device 150 may compare the liquid level to a predetermined threshold value to decide whether to instruct valves or system components to open or otherwise act.

At block 410, the solution 304 is filtered through a sieve as described above. As solution 304 travels through delivery tube 312, it is deposited into sieve 332 to sort out different sizes of insect pupae or remove foreign or unwanted matter. At block 212 of the process 400, solution 304 is delivered to a destination. The destination may be container 336 or container 342 as described in FIG. 3. In some examples this step may include diverting or moving a delivery device to deliver solution 304 to a different container or destination as desired.

Figure 6:
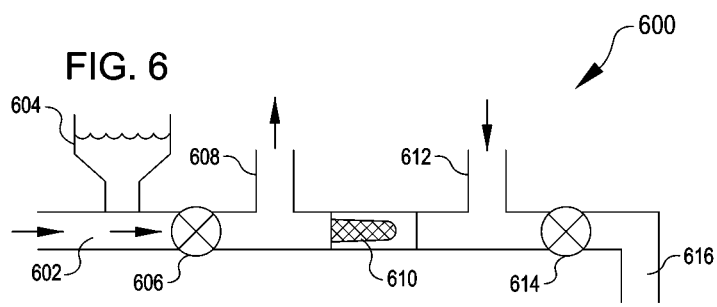

FIG. 6 illustrates an insect pupae transfer system 600 for transferring insect pupae, according to at least one example. The insect pupae transfer system 600 enables transfer of insect pupae in solution from a first location to a second location. The example shown in FIG. 6 relies on a positive pressure to carry insect pupae from the first location to the second location. In particular, the insect pupae transfer system 600 includes a conduit 602, a reservoir 604, a first valve 606, a pupae outlet 608, a sieve 610, a fluid inlet 612, a second valve 614, and a fluid outlet 616. The conduit 602 may provide a conduit for fluid communication between holding tanks, such as holding tank 302 and containers 336 and 342 of FIG. 3. As insect pupae and fluid are introduced into the conduit 602, the insect pupae may be sieved to separate the fluid from the insect pupae. The insect pupae are subsequently backflushed using a second fluid to carry the insect pupae to a destination, such as containers 336 and 342. The second fluid may be driven by pressure to carry the insect pupae to a second location that is positioned vertically higher than the first position where the insect pupae are held.

Functionality described herein may be performed using a computing device (not shown), such as the computing device 350 of FIG. 3. Computing device 350 may send signals to control actuation of fluid inlet 612, first valve 606, and second valve 614 as well as provide communications with additional systems. Such communication and signals may be carried through wired connections or may be carried out over a network, such as the internet or a local network. The computing device is described in further detail with respect to FIG. 5.

The conduit 602 provides a fluid connection between a first location where insect pupae are held and a second location connected to pupae outlet 608 where the insect pupae are to be delivered by the insect pupae transfer system 600. The conduit 602 is also in fluid communication with reservoir 604 upstream of first valve 606 such that when first valve 606 is closed, a flow of fluid and insect pupae passes into the reservoir 604 where the insect pupae may be exposed to a surface of the fluid and not drown during transportation.

Downstream of the first valve 606 pupae outlet 608 provides fluid communication from conduit 602 to the second location, such as a holding container or sieving device for sorting insect pupae. The pupae outlet 608 may include a valve to selectively, as controlled by a computing device, enable pupae to flow to the second location. The flow of liquid and insect pupae introduced into the conduit 602 may not have sufficient pressure to carry the insect pupae to the second location, for example in instances where the second location is positioned vertically higher than the first location or where the second location is at a distance of more than a few meters from the first location, such as across a warehouse or rearing facility. To carry the insect pupae through pupae outlet 608 and on to the second location, a second flow of fluid is introduced to the conduit 602, the second flow of fluid may have a higher pressure than the fluid introduced with the insect pupae.

Downstream of the pupae outlet 608 is a sieve 610 to separate insect pupae from the flow of fluid and insect pupae introduced into the conduit 602. The sieve 610 may have openings smaller than a representative dimension of an insect pupae, such that fluid and debris smaller than the representative insect pupae pass through the sieve 610 while insect pupae are caught and retained at the sieve 610. The fluid and debris that pass through the sieve 610 travel downstream through conduit 602 to fluid outlet 616 when second valve 614 is in an open configuration.

Downstream of the sieve 610 and upstream of the second valve 614 is a fluid inlet 612 where the second flow of fluid is introduced into the conduit 602. The fluid inlet 612 may, in some examples, include a valve for selectively opening and closing fluid inlet 612 as well as providing partial opening, such as to open the valve by fifty percent and allow a fraction of the second fluid flow into the conduit 602. As described above, the second flow of fluid may have a higher pressure, flow rate, or otherwise be configured to carry insect pupae to the second location through the pupae outlet 608. The fluid inlet 612 is upstream of the second valve 614 such that when second valve 614 is closed and the second fluid is introduced into the conduit 602, insect pupae caught by sieve 610 may be backflushed and carried by the second fluid. During the backflush operation, the first valve 606 and second valve 614 are closed such that the second fluid enters the conduit 602 and backflushes the insect pupae through the pupae outlet 608.

During operation, the flow of insect pupae and fluid are initially introduced into the conduit 602. The first valve 606 may be opened, upon receiving a signal from the computer system, to allow the insect pupae and fluid to pass through to sieve 610. The fluid and debris may pass through sieve 610 and past open second valve 614 to fluid outlet 616. The first valve 606 and second valve 614 may be closed, simultaneously or at around the same time, to enable backflushing of the insect pupae through the pupae outlet 608. The first valve 606 and the second valve 614 may be closed for the backflushing to be performed at a regular interval, such as every ten to thirty seconds, or once a minute or more. In some examples, the first valve 606 and the second valve 614 may be instructed to close based on a signal received at a computing device controlling the valves. The signal may include a time period elapsing, as described above, or may include a signal indicating the sieve 610 is loaded with insects, such as an optical sensor positioned within conduit 602 or a flow sensor positioned downstream of sieve 610 detecting a reduction, beyond a predetermined threshold, in the fluid flow rate beyond the sieve 610. For instance, when the fluid flow sensor detects a flow rate downstream of the sieve 610 that is less than a threshold of ninety percent of the flow rate into the conduit 602, the computing device may instruct the first valve 606 and second valve 614 to close to perform a backflush and thereby clear sieve 610. In some examples, the threshold may be less than ninety percent, such as seventy-five percent or even lower.

After closing the first valve 606 and the second valve 614, the second fluid is introduced through the fluid inlet 612 to reverse the direction of flow across the sieve 610 and carry the insect pupae caught by the sieve 610 away from the sieve. Because the first valve 606 is closed, the second fluid and insect pupae are carried though the pupae outlet 608 towards a destination.

Figure 7:
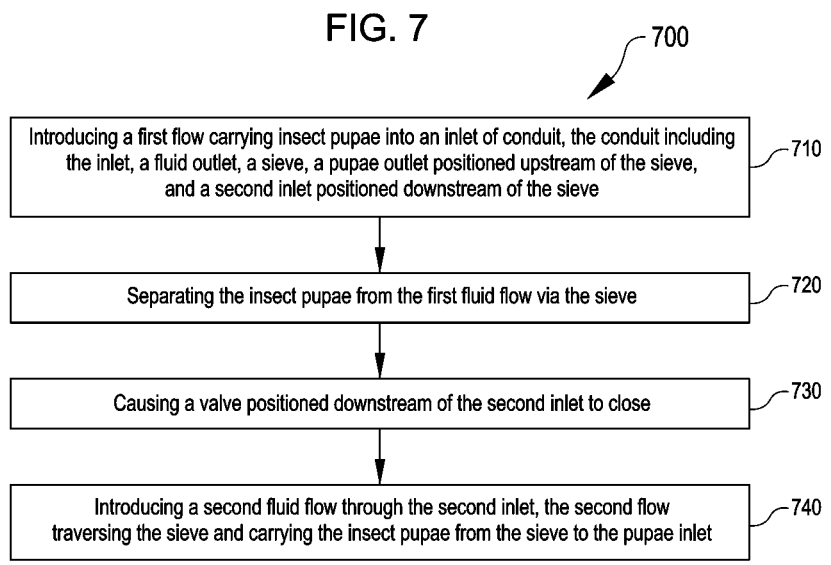

FIG. 7 illustrates a process 700 for transferring insect pupae, according to at least one example. Process 700 for transferring insect pupae may be implemented by a computer device, such as computer device 350 or computer system 500 as described herein. In some examples the processes may also be performed by a human operator.

At block 710, the process 700 includes introducing a first flow carrying insect pupae into an inlet of a conduit, the conduit including the inlet, a fluid outlet, a sieve, a pupae outlet positioned upstream of the sieve, and a second inlet positioned downstream of the sieve. The conduit may be the conduit 602 of FIG. 6, with fluid outlet 616, sieve 610, pupae outlet 608, and second inlet being fluid inlet 612. The first flow of fluid carries the insect pupae through the conduit in a first direction, from an inlet towards the fluid outlet 616. The conduit may provide fluid communication between a first location, such as a holding tank, and a second location, such as a storage container for insect pupae.

At block 720, the process 700 includes separating the insect pupae from the first fluid flow via the sieve. The sieve may be the sieve 610 of FIG. 6. The sieve 610 may have openings smaller than a representative dimension of an insect pupae, such that fluid and debris smaller than the representative insect pupae pass through the sieve 610 while insect pupae are caught and retained at the sieve 610.

At block 730, the process 700 includes causing a valve positioned downstream of the second inlet to close. The valve may be valve 614 that closes off fluid outlet 616 such that the fluid flowing through the conduit 602 cannot proceed past sieve 610. In some examples, the process 700 may also include causing a valve positioned upstream of the pupae outlet to close. In some examples, this is performed by a computer device instructing valves 606 and 614 to close, preventing the fluid flow and insect pupae from entering the conduit 602 and stopping the flow of liquid through the sieve 610. The valve, or in some examples both valves, may be actuated in response to an elapsed time interval, for example that results in valves 606 and 614 closing at a regular time interval for backflushing the sieve 610 to carry insect pupae out through pupae outlet 608. In some examples, a sensor may detect the presence of insect pupae at the sieve, as described above, and cause the computing device to convey a signal causing the valves to close and to backflush the system.

At block 740, the process 700 includes introducing a second fluid flow through the second inlet, the second flow traversing the sieve and carrying the insect pupae from the sieve to the pupae inlet. The second inlet may be the fluid inlet 612. The second fluid flows across the sieve 610 in a direction opposite from a direction of flow of the fluid and insect pupae initially. The second fluid flow carries insect pupae away from the sieve 610 and through pupae outlet 608, which is the only open and available channel for fluid to flow through once valves 606 and 614 are closed. The second fluid flow may be introduced by a computing device causing a valve of the fluid inlet 612 to open, to allow the second fluid to flow into conduit 602. The fluid inlet 612 may be closed when valves 606 and 614 are opened such that fluid flows out through fluid outlet 616.

FIG. 5 illustrates examples of components of computer system 500, according to at least one example. Computer system 500 may be a single computer such as a user computing device or can represent a distributed computing system such as one or more server computing devices. Computer system 500 is an example of the computing device 150, 350 described above with respect to systems 100, 300.

Computer system 500 may include at least processor 502, memory 504, storage device 506, input/output peripherals (I/O) 508, communication peripherals 510, and interface bus 512. Interface bus 512 is configured to communicate, transmit, and transfer data, controls, and commands among the various components of computer system 500. Memory 504 and storage device 506 include computer-readable storage media, such as Random Access Memory (RAM), Read ROM, electrically erasable programmable read-only memory (EEPROM), hard drives, CD-ROMs, optical storage devices, magnetic storage devices, electronic non-volatile computer storage, for example Flash® memory, and other tangible storage media. Any of such computer-readable storage media can be configured to store instructions or program codes embodying aspects of the disclosure. Memory 504 and storage device 506 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with computer system 500.

Further, memory 504 includes an operating system, programs, and applications. Processor 502 is configured to execute the stored instructions and includes, for example, a logical processing unit, a microprocessor, a digital signal processor, and other processors. Memory 504 or processor 502 can be virtualized and can be hosted within another computing system of, for example, a cloud network or a data center. I/O peripherals 508 include user interfaces, such as a keyboard, screen (e.g., a touch screen), microphone, speaker, other input/output devices, and computing components, such as graphical processing units, serial ports, parallel ports, universal serial buses, and other input/output peripherals. I/O peripherals 508 are connected to processor 502 through any of the ports coupled to interface bus 512.

Communication peripherals 510 are configured to facilitate communication between computer system 500 and other computing devices over a communications network and include, for example, a network interface controller, modem, wireless and wired interface cards, antenna, and other communication peripherals.

While the present subject matter has been described in detail with respect to specific examples thereof, it will be appreciated that those skilled in the art, upon attaining an understanding of the foregoing may readily produce alterations to, variations of, and equivalents to such examples. Accordingly, it should be understood that the present disclosure has been presented for purposes of example rather than limitation, and does not preclude inclusion of such modifications, variations, or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more examples of the present subject matter. Any suitable programming, scripting, or other type of language or combinations of languages may be used to implement the teachings contained herein in software to be used in programming or configuring a computing device.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, or steps. Thus, such conditional language is not generally intended to imply that features, elements or steps are in any way required for one or more examples or that one or more examples necessarily include logic for deciding, with or without author input or prompting, whether these features, elements or steps are included or are to be performed in any particular example.

The terms "comprising," "including," "having," and the like are synonymous and are used inclusively, in an open-ended fashion, and do not exclude additional elements, features, acts, operations, and so forth. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" or "substantially" includes within a tolerance of ±0.01%, ±0.1%, ±1%, ±2%, ±3%, ±4%, ±5%, ±8%, ±10%, ±15%, ±20%, ±25%, or as otherwise known in the art.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

What is claimed is:

1. A method comprising:
   introducing a first fluid flow carrying insect pupae into an inlet of conduit, the conduit including the inlet, a fluid outlet, a sieve, a pupae outlet positioned upstream of the sieve, and a second inlet positioned downstream of the sieve;
   separating the insect pupae from the first fluid flow via the sieve;
   causing a valve positioned downstream of the second inlet to close; and
   introducing a second fluid flow through the second inlet, the second fluid flow traversing the sieve and carrying the insect pupae from the sieve to the pupae outlet.

2. The method of claim 1, wherein the sieve defines a plurality of openings, a dimension of each of the plurality of openings less than a width of a representative insect pupae.

3. The method of claim 1, wherein the first fluid flow is in a first direction across the sieve and the second fluid flow is in a second direction across the sieve, the second direction different from the first direction.

4. The method of claim 1, wherein the valve is a second valve, and the method further comprising causing a first valve positioned upstream of both the sieve and the pupae outlet to close before introducing the second fluid flow.

5. The method of claim 1, wherein causing the valve to close comprises:
   receiving, at a computing device, a signal indicating that a predetermined period of time has elapsed; and
   conveying, from the computing device, a signal to the valve instructing the valve to close.

6. The method of claim 5, further comprising causing the valve to open after a second predetermined period of time has elapsed.

7. The method of claim 1, wherein causing the valve to close comprises:
   receiving, at a computing device, a signal indicating a presence of insect pupae at the sieve; and
   conveying, from the computing device, a signal to the valve instructing the valve to close.

* * * * *